(12) United States Patent
Brunfeld et al.

(10) Patent No.: US 6,262,432 B1
(45) Date of Patent: *Jul. 17, 2001

(54) HIGH SPEED SURFACE INSPECTION OPTICAL APPARATUS FOR A REFLECTIVE DISK USING GAUSSIAN DISTRIBUTION ANALYSIS AND METHOD THEREFOR

(75) Inventors: Andrei Brunfeld, Bat-Yam; Joseph Shamir, Haifa; Gregory Toker, Jerusalem; Liviu Singher, Haifa; Ilan Laver; Ely Pekel, both of Kefar Saba, all of (IL)

(73) Assignee: Brown & Sharpe Surface Inspection Systems, Inc., North Kingstown, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/985,630

(22) Filed: Dec. 3, 1992

(51) Int. Cl.[7] ................................................. G01H 21/88
(52) U.S. Cl. .................... 250/559.45; 356/239.1
(58) Field of Search .................... 250/234–236, 250/562, 563, 571, 572, 559.45, 559.48, 559.49; 356/238, 239, 429–431, 237.1, 237.2, 239.1; 364/507; 209/588

(56) References Cited

U.S. PATENT DOCUMENTS

| | | | |
|---|---|---|---|
| 3,836,261 | * | 9/1974 | Clarke .................................. 250/571 |
| 4,376,583 | * | 3/1983 | Alford .................................. 250/572 |
| 4,505,585 | * | 3/1985 | Yoshikawa et al. .................. 356/237 |
| 4,924,086 | * | 5/1990 | Weber .................................. 250/235 |
| 4,954,723 | * | 9/1990 | Takahashi et al. .................... 250/563 |
| 5,031,112 | * | 7/1991 | Sakai et al. .......................... 364/507 |
| 5,135,305 | * | 8/1992 | Uto et al. ............................. 250/563 |

* cited by examiner

Primary Examiner—Stephone B. Allen
(74) Attorney, Agent, or Firm—Wolf, Greenfield & Sacks, P.C.

(57) ABSTRACT

An optical inspection apparatus operates at high speed at very high resolution for detecting defects in reflective disks in a production environment. These reflective disks are of the type commonly used as disk platters in hard disk drives. This apparatus uses a laser which provides a light beam directed to a polygon scanner, which provides a linear scan of the beam along a radius on both sides of the disk by using two mirrors to direct the light beam. The disk to be inspected is rotated such that its entire surface passes the scan path of the light beam. The light beam is reflected off the reflective disk, and returns to the scanning optics and the polygon scanner in a path coincident with the transmitted light beam. The reflected light beam is distinguished from the transmitted light beam by using a beam splitter to direct the reflected light beam to a parallel detector array, which detects changes in the nominal Gaussian distribution of the light beam that correspond to defects in the surface of the reflective disk above a programmable threshold level. This parallel detection method allows the inspection apparatus to identify defects much smaller than the diffraction limits of the optics used, and will accurately identify changes in the light beam caused by defects in the disk. An automatic disk handler loads untested disks into the apparatus and unloads and sorts tested disks according to the results of the inspection.

96 Claims, 8 Drawing Sheets

HIGH SPEED SURFACE INSPECTION OPTICAL APPARATUS FOR A REFLECTIVE DISK USING GAUSSIAN DISTRIBUTION ANALYSIS AND METHOD THEREFOR

RELATED APPLICATIONS

This patent application is related to three other U.S. patent applications entitled: "High Speed Optical Inspection Apparatus and Method", "High Speed Optical Inspection Apparatus for a Transparent Disk and Method Therefor", and "High Speed Optical Inspection Apparatus for a Transparent Flat Panel and Method Therefor" which are assigned to the same assignee as this patent application and which are filed on the same date as the date of this patent application.

FIELD OF THE INVENTION

This invention generally relates to optical apparatus and methods, and relates, more specifically, to an optical inspection apparatus and method for detecting faults in a flat, polished reflective disk, such as those commonly used as platters for hard disk drives. This apparatus inspects with high resolution at high speed with automatic handling of the disk to allow the apparatus to be used effectively in a production inspection environment.

DESCRIPTION OF THE PRIOR ART

Disks for hard disk drives require a surface that is flat to a high degree of accuracy, and that is free from defects such as scratches and chips. Some optical inspection systems have been used with limited success in inspecting reflective disks, but do not provide the accuracy or speed that is needed in a production environment.

Dark field microscopes and scatterometers are inspection apparatus well-known in the art. A dark field microscope can somewhat accurately locate surface defects, but takes too long to inspect to be effectively used in a production environment. A scatterometer is faster than a dark field microscope, but has less accuracy (detects fewer defects). Both the dark field microscope and the scatterometer have low detection sensitivity to shallow defects or defects that have a depth less than the wavelength of the light used, which cause a phase shift in the light beam but do not diffuse (scatter) the light in different directions. An interferometer, which is well-known in the art, is suitable to detecting phase shifts, but takes substantial time and effort to set up, limiting its use to laboratory environments.

The inherent limitations of the prior art inspection systems have limited their use in industrial production environments. Indeed, the most common inspection method used in a production environment is a manual, visual inspection by human inspectors, which hold the disk in their hands and move the disk in ambient or special light looking for the presence of scratches, chips and other defects. This inspection method is labor intensive, relatively slow, and subject to human errors such as missed defects which the human eye cannot easily distinguish.

Therefore, there existed a need to provide a high speed optical inspection system and method which has a high sensitivity to defects which can be used to inspect reflective disks in a production environment. This inspection system includes automatic handling of the disks, high speed inspection, and high resolution to detect defects smaller that the spot size of the beam and/or more shallow than the wavelength of light used. The increased speed of this apparatus increases throughput of the production system, and assures that any mistakes or defects introduced by human inspectors is eliminated.

SUMMARY OF THE INVENTION

It is an object of this invention to provide a high-speed optical inspection apparatus and method suitable for production testing of reflective disks.

It is another object of this invention to provide a high speed optical inspection apparatus and method which is computer-controlled using an IBM PC-AT computer or equivalent.

It is a further object of this invention to provide a high speed optical inspection apparatus and method with surface defect detection which has a high speed optical scanner to provide linear movement of the beam across a radius of the disk, and a disk actuator to rotate the disk, thereby positioning each portion of the disk in the path of the linear movement of the beam, thereby completely inspecting the entire face surface of the disk.

It is still another object of this invention to provide a high speed optical inspection apparatus and method with edge inspection using a light source and linear Charge-Coupled Device (CCD) cameras which scan the edge of the disk as it is rotated during surface inspection.

It is yet another object of this invention to provide a high speed optical inspection apparatus and method which has an Automatic Disk Handler for automatically loading the disks into the apparatus and for automatically unloading the disks from the apparatus.

It is a still further object of this invention to provide a high speed optical inspection apparatus and method which detects both phase and amplitude changes of the light beam using multiple detectors to sense changes in the nominal Gaussian distribution of the light beam.

It is yet another object of this invention to provide a high speed optical inspection apparatus and method which has a trigger detector within the path of the scanning light beam to provide a signal to synchronize the controlling computer to the scan of the light beam.

According to the preferred embodiment of the present invention, an optical inspection apparatus for inspecting a reflective disk is provided. This inspection apparatus is controlled by an IBM PC-AT computer or equivalent, and has a typical color monitor, printer and keyboard. An Optical Inspection Assembly is provided which comprises a Surface Inspection Assembly and an Edge Inspection Assembly. The Surface Inspection Assembly nominally comprises a laser light source which transmits a light beam, a high-speed Optical Scanner, Scanning Optics, a beam splitter, optional Detection Optics, and a Parallel Detector Array within a Detector. In this configuration the light beam in the Surface Inspection Assembly originates in the laser, is transmitted through a filter, and is transmitted to the Optical Scanner, which reflects the light beam off the moving polygonal scanner head, causing the light beam to sweep across the Scanning Optics.

In the preferred embodiment of the present invention, the inspection apparatus is used to inspect both sides of the reflective disk within the same scan. This is accomplished by placing the reflective disk near the center of the scanning beam sweep, with its face normal to the direction of the sweep. Two mirrors are placed at 45 degree angles with respect to the two faces of the disk such that the Optical Scanner beam is reflected onto the two faces. The Scanning Optics and the mirrors focus the Optical Scanner beam on the two faces of the reflective disk. As the Optical Scanner beam begins its scan, the first mirror reflects the beam to the outer edge of the first face of the disk. The reflective face of the disk reflects the beam back to the mirror, which reflects the beam back to the Optical Scanner. This reflected beam is distinguished from the transmitted beam using a beam splitter between the laser and the Optical Scanner. The reflected beam is then projected on the Parallel Detector Array, which detects defects in the disk above a programmable threshold. This array is typically a matrix of photodiodes or Charge-Coupled Devices (CCDs) upon which the light beam is projected. This matrix configuration provides a two dimensional Gaussian response with respect to light intensity (amplitude). Any defect in the disk deflects light from the Parallel Detector Array (causing a change in the nominal light level) or shifts its phase (causing a change in the Gaussian distribution), both of which are detected by the processing electronics coupled to the Parallel Detector Array. Thus the processing electronics simply look for changes in the nominal level or distribution of the Gaussian response provided by the Parallel Detector Array in response to a nominal light beam, which changes correspond to surface defects an a reflective disk.

As the Optical Scanner beam moves, the beam on the disk moves from outside to inside on this first side of the disk. The first side of the disk is completely scanned when the Optical Scanner beam has traveled about half of its scan distance. Near the center of the scan the Optical Scanner beam contacts the outside edge of the disk. As the Optical Scanner beam continues its scan, the second mirror reflects the Optical Scanner beam, beginning at the inside of the disk on the second face of the disk, and moves from inside to outside. By the time the Optical Scanner beam has completed one linear scan, both sides of the disk have been inspected along the scan line. The disk is then rotated to the next position, and the scanning continues in like manner until the entire surface of both sides of the disk have been simultaneously inspected. The computer controls the rotation of the disk to assure the entire surface is scanned. At the same time the disk is rotating, the Edge Inspection Assembly simultaneously inspects the outer edges of the disk for defects above a programmable threshold. If either the Surface Inspection Assembly or the Edge Inspection Assembly detects a defect greater than their programmed thresholds, a fault signal is sent to the computer to indicate that the disk failed the inspection. The Automatic Disk Handler then sorts the tested disks according to the pass or fail results of the inspection.

In the second embodiment of the present invention, the reflective disk is placed normal to the Optical Scanner beam, and no mirrors are used. The reflective disk reflects the beam, which is distinguished from the transmitted beam using a beam splitter between the laser and the Optical Scanner. The reflected beam is then projected on the Parallel Detector Array, which detects defects in the disk above a programmable threshold. With this configuration, only one side of the disk is inspected at a time, requiring the automatic disk handler to turn the disk over after the first side is inspected for inspection of the second side, or requiring two separate scanning systems to inspect both sides simultaneously.

The foregoing and other objects, features and advantages will be apparent from the following description of the preferred embodiments of the invention as illustrated in the accompanying drawings.

DESCRIPTION OF THE PREFERRED EMBODIMENT

Figure 1:
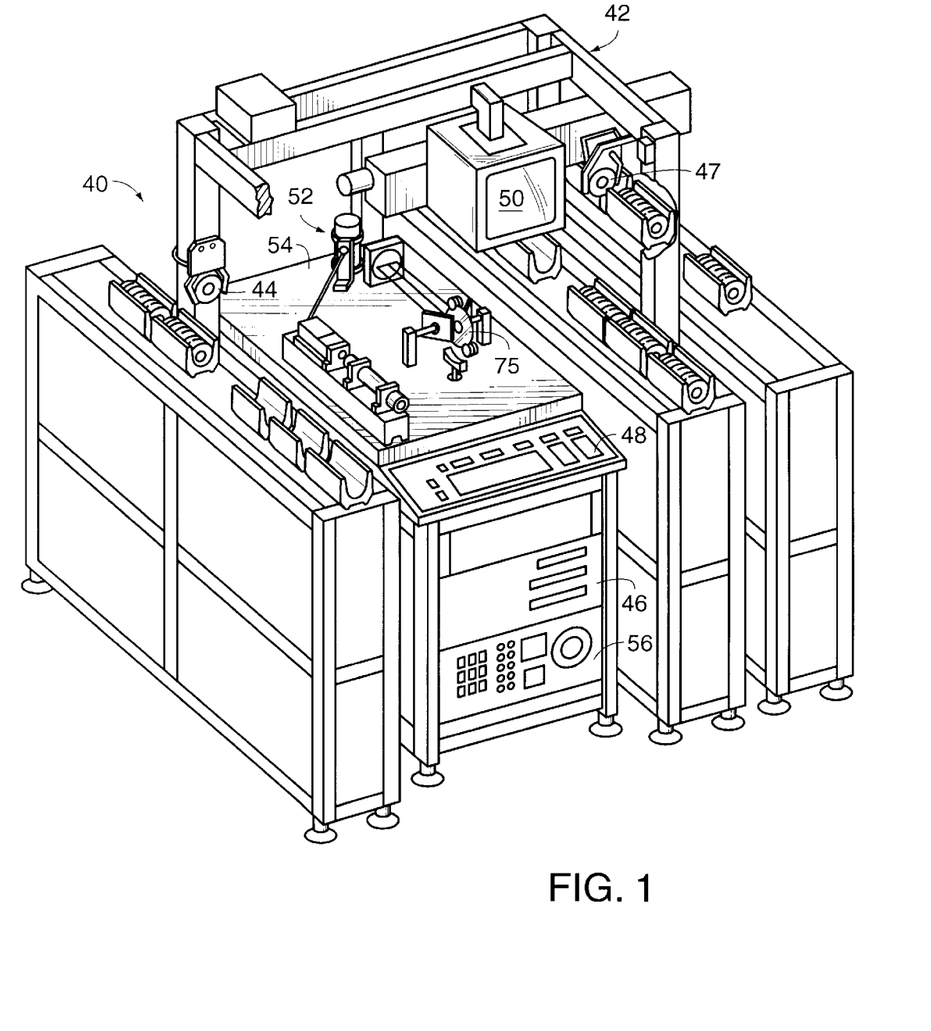
FIG. 1 is a perspective view of the optical inspection apparatus of the present invention.
Figure 2:
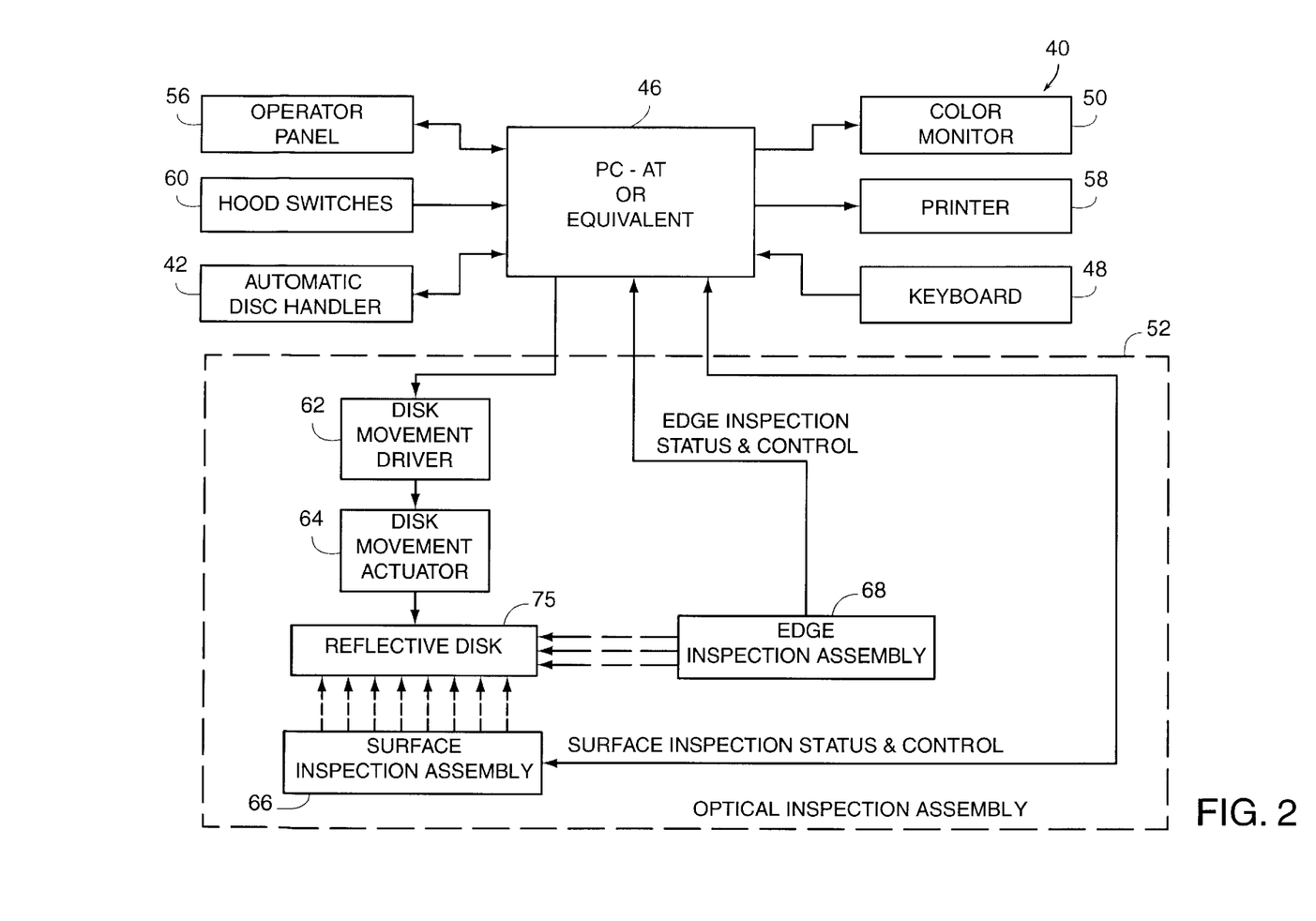
FIG. 2 is a block diagram of the optical inspection apparatus of FIG. 1.

FIG. 1 shows the optical inspection apparatus 40 of the present invention, comprising an IBM compatible PC-AT computer 46 or equivalent, a keyboard 48, a color monitor 50, an operator panel 56, an Optical Inspection Assembly 52 located on table 54, and an Automatic Disk Handler 42 (typically a robot) to automatically load and unload the disk to be inspected (44, 75, and 47) into the Optical Inspection Assembly 52. FIG. 2 is the block diagram of the apparatus 40 of the present invention, with numbers that correspond to numbers in FIG. 1 representing the same components. The apparatus shown in FIG. 2 includes a printer 58, and hood switches 60 for detecting when the apparatus 40 is ready for operation. These hood switches 60 act as safety devices, inhibiting operation of the apparatus 40 until the apparatus 40 is in the correct configuration with all hoods secured properly. The Optical Inspection Assembly 52 comprises a Disk Movement Driver 62, a Disk Movement Actuator 64, a Surface Inspection Assembly 66, an Edge Inspection Assembly 68, and a Reflective Disk 75.

The Automatic Disk Handler 42 first loads the Reflective Disk 75 into the Optical Inspection Assembly 52. The Surface Inspection Assembly 66 then begins its scan of the surface of the Reflective Disk 75. At the same time the Edge Inspection Assembly 68 begins inspection of the outer edges of the Reflective Disk 75. Both the Surface Inspection Assembly 66 and the Edge Inspection Assembly 68 perform only a linear inspection, and thus depend on the Disk Movement Actuator 64 to rotate the Reflective Disk 75 such that the entire surface is inspected by the Surface Inspection Assembly 66, and such that the entire edge is inspected by the Edge Inspection Assembly 68.

The Surface Inspection Assembly 66 and the Edge Inspection Assembly 68 both have programmable thresholds that determine the characteristics of allowable defects. If either of these assemblies detects a defect greater than the programmed threshold, a fault signal is sent to the computer 46 to indicate that the inspection failed. The computer 46 causes the Automatic Disk Handler 42 to place good disks (those that pass inspection) in one place, and to place bad disks (those that fail inspection) in a different place. In a fully automated system, an automated cart or conveyer would deliver uninspected disks and take away both good and bad inspected disks as the apparatus 40 requires.

Figure 3:
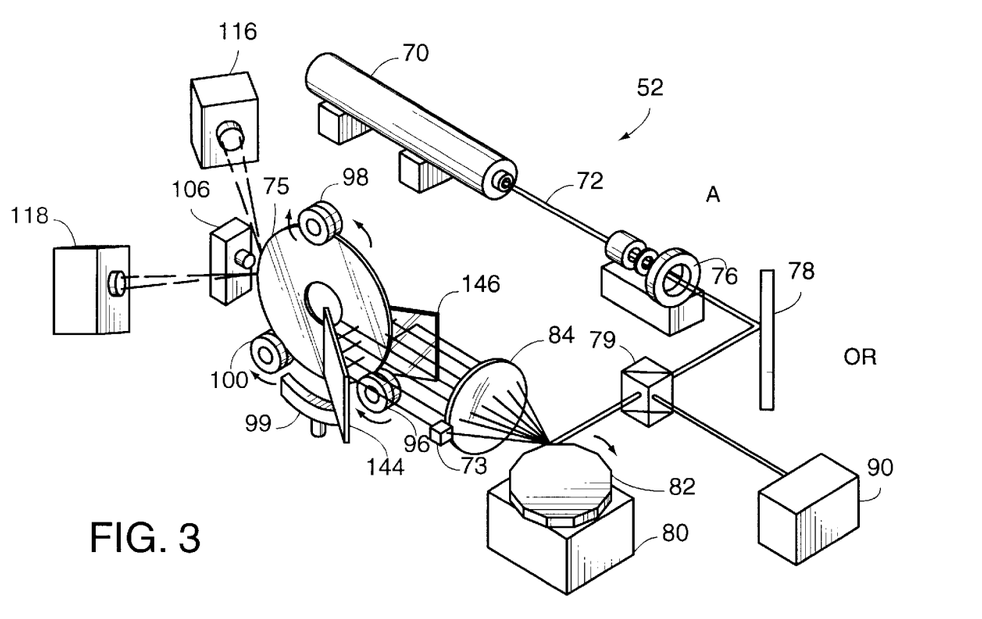
FIG. 3 is a perspective view of the Optical Inspection Assembly used in the apparatus shown in FIG. 1.

The Optical Inspection Assembly 52 for the first embodiment of the present invention is shown in FIG. 3. A laser 70 provides the light beam 72 used to inspect the Reflective Disk 75. The laser 70 must have a minimum spatial and temporal coherence greater than the defects to be measured. The coherence of the laser 70 is related to its optical Signal to Noise (S/N) ratio, while the power of the laser 70 is related to its electrical S/N ratio. The light beam 72 passes through Filter Optics 76, which increases the spatial coherence of the beam 72 and shapes and directs the beam 72 to the mirror 78, which directs the beam 72 to Optical Scanner 80. Optical Scanner 80 has a rotating polygonal head 82 with reflective faces. The mirror 78 directs the beam 72 to the rotating polygonal head 82, which causes the beam 72 to sweep across the Scanning Optics 84. If the polygonal head 82 rotates clockwise as shown, the sweep of the beam 72 will be from left to right on the Reflective Disk 75.

Figures 4, 5A, 5B:
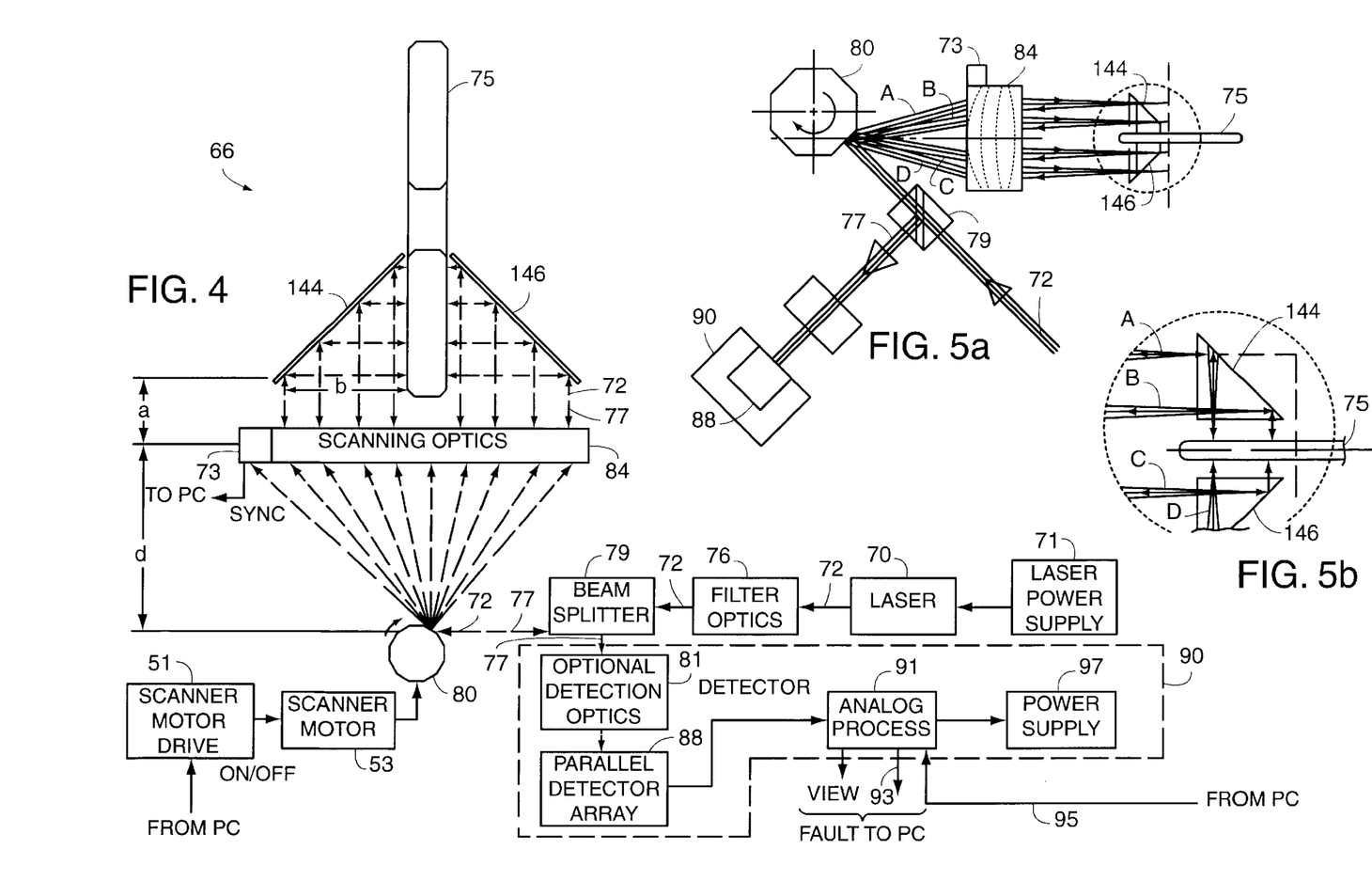
FIG. 4 is a block diagram of the Surface Inspection Assembly portion of the Optical Inspection Assembly shown in FIGS. 2 and 3.
FIG. 5a is a top view of the Optical Scanner and optics function in the Surface Inspection Assembly shown in FIG. 4 according to the first embodiment of the apparatus shown in FIG. 1.
FIG. 5b is an enlarged view of the circle in FIG. 5a showing how the beam is focused on the surface of the reflective disk and reflected back.

In the first embodiment of the present invention as shown in FIGS. 3 and 4, both sides of the Reflective Disk 75 are inspected in the same scan by using two mirrors 144 and 146 to scan both sides of Reflective Disk 75 in one scan of beam 72. The mirrors 144 and 146 are placed at 45 degree angles with respect to the two faces of the Reflective Disk 75 so the reflected light beam 77 will be coincident with the transmitted light beam 72. In this configuration there is no separate Detection Optics, but the light beam 72 is reflected back to the Scanning Optics 84, which directs the reflected beam 77 (still coincident with the transmitted beam 72) to the Optical Scanner 80, then to a Beam Splitter 79. The Beam Splitter 79 directs the reflected beam 77 to the Parallel Detector Array 88 within Detector 90.

Figure 10A:
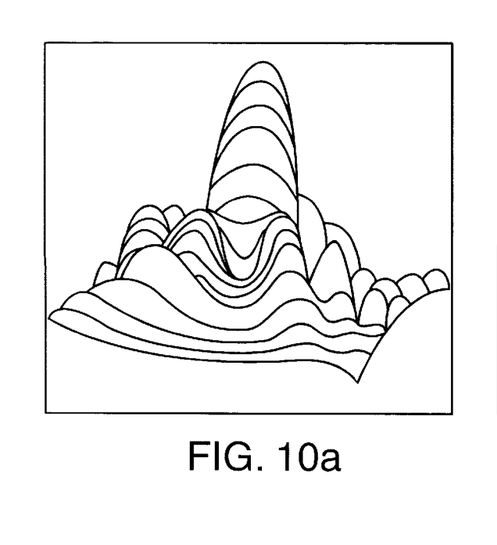
FIG. 10a is a three dimensional representation of a typical Gaussian distribution of light intensity (amplitude).
Figure 10B:
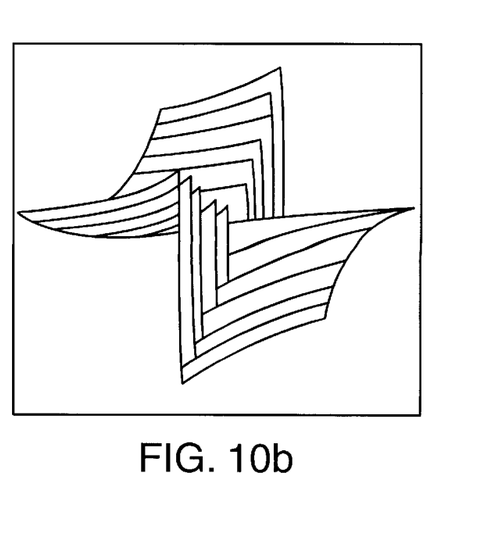
FIG. 10b is a three dimensional representation of a typical Gaussian distribution of light phase.
Figure 11A:
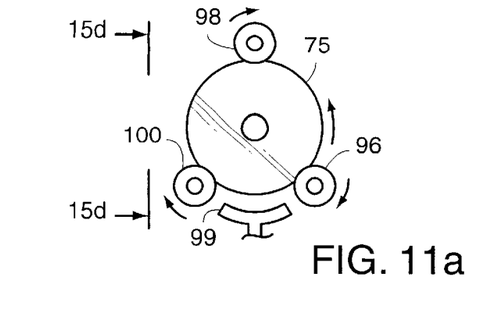
FIG. 11a is an elevational view of the disk of FIG. 3 showing the roller configuration which rotates the disk during inspection.
Figure 11B:
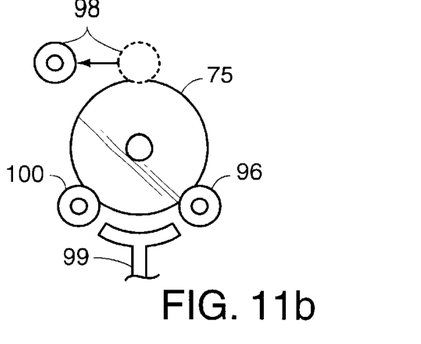
FIG. 11b is an elevational view of the disk and rollers of FIG. 11a showing how the top roller moves to facilitate loading and unloading of the disk by the Automatic Disk Handler.
Figures 11C, 11D, 12, 12B:
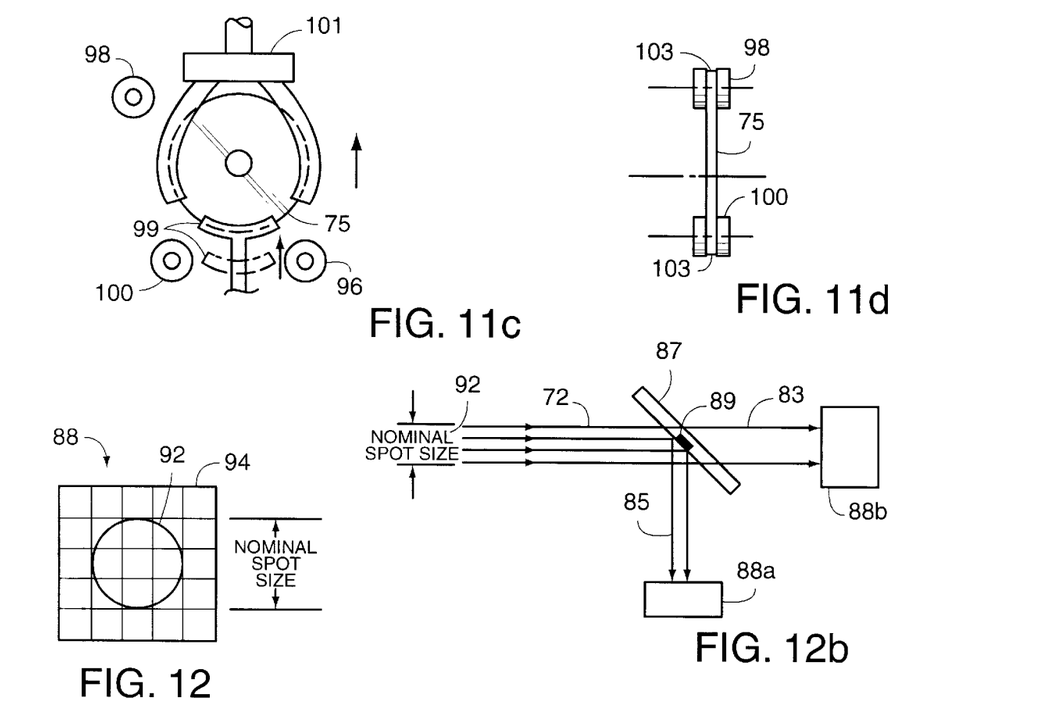
FIG. 11c is an elevational view of the disk and rollers of FIG. 11b showing how the movement of the roller shown in FIG. 11b and the operation of the lifter allow the Automatic Disk Handler to load and unload the disk into the apparatus of FIG. 3.
FIG. 11d is a side view of two of the rollers and the disk shown in FIG. 11a taken along the line 11d—11d showing the slot in the rollers for holding the disk in place during rotation.
FIG. 12 is a front view of one specific configuration of the Parallel Detector Array which detects changes in the amplitude and/or phase of the Optical Scanner beam.
FIG. 12b is a top view of the optics function of an alternative parallel detection configuration which detects changes in the amplitude and/or phase of the Optical Scanner beam.

One specific implementation of the Parallel Detector Array 88 is shown in more detail in FIG. 12. An array of light sensitive devices 94 is provided, typically a photodiode array. Each light sensitive device 94 provides an electrical signal proportional to the intensity of light it detects. A nominal beam spot 92 is shown, which is smaller than the matrix as shown. This type of a spot 92 of laser light on Parallel Detector Array 88 causes a two-dimensional response with respect to intensity or amplitude, which is represented in FIG. 10a. Likewise, this type of spot 92 causes a two-dimensional response with respect to changes of phase, which is represented in FIG. 10b. The changes of phase will create an interference pattern between the center and outer rim of the beam 72, causing a change in the ideal Gaussian distribution.

Figure 12A:
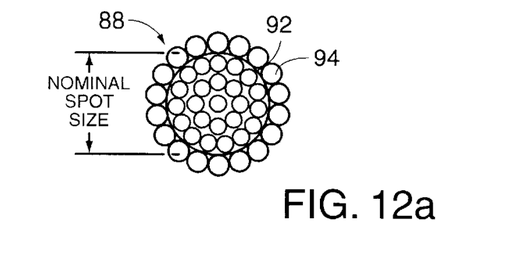
FIG. 12a is a front view of another specific configuration of the Parallel Detector Array which detects changes in the amplitude and/or phase of the Optical Scanner beam.
Figure 12C:
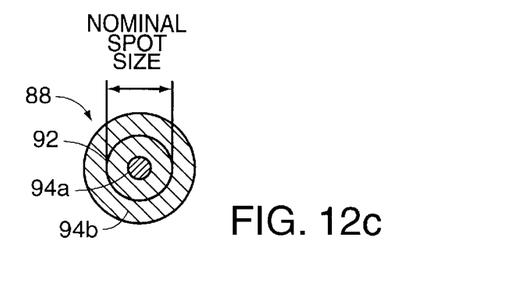
FIG. 12c is a front view of another specific configuration of the Parallel Detector Array which detects changes in the amplitude and/or phase of the Optical Scanner beam.

Note that the light sensitive devices 94 of Parallel Detector Array 88 could also be an array of CCDs, and could be arranged in any physical configuration, such as circular or concentric rings of individual detectors, as shown in FIG. 12a. In addition, two concentric ring detectors in the configuration shown in FIG. 12c could be used to form Parallel Detector Array 88. Detector 94a detects the center portion of the beam, while detector 94b detects the outer portion of the beam, which has nominal spot size 92 as shown.

FIG. 12b shows an alternative arrangement which uses two Parallel Detector Arrays 88. Beam 72 has a nominal spot size 92 as shown. Beam 72 is projected onto a transparent substrate 87 which has a small reflective portion 89, and is positioned at a 45 degree angle with respect to the beam 72 as shown. In this manner the center portion 85 of beam 72 is reflected off the reflective portion 89 of transparent substrate 87 to a Parallel Detector Array 88a as shown in the figure. The outer portion 83 of the beam 72 passes through the transparent substrate 87 onto a second Parallel Detector Array 88b. In this manner the two Parallel Detector Arrays 88a and 88b act in parallel to detect any change in the nominal Gaussian distribution of light within beam 72.

Note that the Parallel Detector Arrays 88a and 88b shown in FIG. 12b could be replaced with a single detector, since the two detectors 88a and 88b act in parallel, and can therefore detect with only two sensors changes in the nominal Gaussian distribution of the beam 72. Neither the number, type of device used nor the physical arrangement of these devices is critical to this invention. The primary inventive feature regarding the Parallel Detector Array 88 is the use of more than one optical detector in parallel to detect changes in a nominally Gaussian distribution of light within the spot of the optical beam 72.

By measuring changes in the Gaussian distribution of light, the apparatus 40 of the present invention has a much higher resolution than prior art optical inspection systems, which are limited by the diffraction limits of the optics and specific configuration of the system. By measuring changes in the Gaussian distribution of the beam 72, the apparatus 40 measures changes in the electromagnetic fields in a general point in space, which therefore removes the classical diffraction limit experienced by prior art systems. Since the Parallel Detector Array 88 can detect changes in both phase and amplitude of the nominal Gaussian distribution of light (phase changes are detected by interference between the center and rim of the beam), a change in the surface characteristics caused by even a very narrow or shallow defect will interfere with the rest of the field, and will be detected. This allows the lateral resolution of the apparatus 40 to be from 100 to 1000 times greater than the diffraction limit, since phase changes are detected as well as amplitude changes. In addition, the longitudinal sensitivity within the diffraction limit is interferometric, while the adjustment sensitivity is only dependent on the depth of field. These features provide for a highly sensitive inspection apparatus 40, which can detect any changes of the optical characteristics of the inspected surface on the order of $\frac{1}{100}$ to $\frac{1}{1000}$ of the diffraction limit in all three axes.

FIG. 4 shows the configuration of the Surface Inspection Assembly 66 shown in FIG. 2 used in the Optical Inspection Assembly 52. Note that many of the numbers in FIG. 4 correspond to components shown in FIG. 3. The laser 70 is powered by a Laser Power Supply 71, and provides beam 72, which passes through Filter Optics 76. The mirror 78 of FIG. 3 is not shown in FIG. 4. The light beam 72 contacts the Optical Scanner 80, which provides a linear scanning action of the beam 72 across Trigger Detector 73 and Scanning Optics 84. Trigger Detector 73 is placed at the beginning position of the scan path of beam 72, and provides an electrical SYNC signal to the computer 46 when the beam 72 contacts it to synchronize the sweep of beam 72 with the rotation of the Reflective Disk 75 and the output of Detector 90. Note that the Optical Scanner 80 can be switched on or off by the computer 46 giving the appropriate command to the Scanner Motor Driver 51, which controls the Scanner Motor 53. Also note that the Trigger Detector 73 can be mounted anywhere within the scan path of beam 72. In the configuration illustrated in the figures, Trigger Detector 73 is mounted on the side of the Scanning Optics 84. The Trigger Detector 73 could, in the alternative, be placed in the scan path of beam 72 next to the Reflective Disk 75. By placing the Trigger Detector 73 next to the Scanning Optics 84, no optic field of Scanning Optics 84 is taken by Trigger Detector 73.

As shown in FIG. 4, the angle sweep of Optical Scanner 80 is converted by the Scanning Optics 84 to a sweep of parallel beams, each contacting the Reflective Disk 75 normal to its surface after reflecting off the mirrors 144 and 146. The beam 72 is reflected by the face of the Reflective Disk 75 back to mirrors 144 and 146, through Scanning Optics 84 to Optical Scanner 80 in a path coincident with the transmitted beam 72. The reflected beam 77 is distinguished from the transmitted beam 72 by using a beam splitter 79 which directs each beam to the Parallel Detector Array 88 within Detector 90. The nominal Gaussian output of Parallel Detector Array 88 is processed by analog circuitry in the Analog Process block 91, which is powered by Power Supply 97. Analog Process 91 receives a threshold control signal 95 from the computer 46 and detects any change in the Gaussian distribution of beam 72 which corresponds to a defect greater than the programmed threshold. When such a defect occurs, the Analog Process 91 signals the computer 46 that the inspection failed by asserting a Fault signal 93. The computer 46 will then nominally abort the inspection of the Reflective Disk 75, and cause the failed disk to be placed in the area of bad disks by the Automatic Disk Handler 42.

FIG. 5*a* clearly represents the operation of the Scanning Optics 84 and the Beam Splitter 79 of the Surface Inspection Assembly 66 shown in FIG. 4. With this configuration, the beam 72 is reflected off the Optical Scanner 80, and first contacts the Trigger Detector 73, then continues to scan across the Scanning Optics 84.

Beam 72 first comes in contact with Scanning Optics 84 on the left side of the Scanning Optics 84, as represented by A in FIG. 5*a*. The beam A contacts the mirror 144 as shown, which focuses beam A on the surface of Reflective Disk 75, which reflects the beam A back along a path coincident with the transmitted beam A. This is shown in more detail in FIG. 5*b*. This reflected beam 77 travels coincident with the transmitted beam 72 until it contacts the Beam Splitter 79, which directs the reflected beam 77 to the Parallel Detector Array 88 within the Detector 90.

As the Optical Scanner beam 72 continues its sweep, it will come to the position shown by beam B, then to the position shown by beam C, and eventually to the position shown by beam D. Note that for each position of the beam 72, a different spot on the Reflective Disk 75 is in the path of the beam 72, and the resulting reflected beam 77 is projected onto the Parallel Detector Array 88 by the Beam Splitter 79 as shown. Note that this method can only be accomplished by placing the Optical Scanner 80 at a distance d from Scanning Optics 84 equal to the focal length of Scanning Optics 84. The surface of the Reflective Disk 75 is located at this same distance from the Scanning Optics 84 after reflection in mirrors 144 and 146. In other words, the distance a+b as shown in FIG. 4 must equal the distance d. Since the Scanning Optics 84 also plays the role of Detection Optics due to the reflected beam 77, the size of the beam 72 at the Optical Scanner 80 is the same as the size of the beam 72 at the Parallel Detector Array 88. Note that Optional Detection Optics 81 may be used for magnification, to correct beam wandering, or for other purposes as required.

As the scanning of beam 72 takes place along a linear radius of both faces of the Reflective Disk 75, the Reflective Disk 75 is rotated one complete revolution to assure the entire disk surface is inspected. While this rotation of the disk takes place, the outer edges of the disk are inspected for defects using the Edge Inspection Assembly 68, shown in detail in FIG. 7. The Edge Inspection Assembly 68 is comprised of an Outer Radius Inspection Assembly 128. Within Outer Radius Inspection Assembly 128, a Power Supply 102 powers a light source 104, which passes through Projection Optics 106 to the outer edge of the Reflective Disk 75 as shown. Each disk nominally has two beveled edges 108 and 110 and a flat edge 109 on its outer edge as shown, and two beveled edges 112 and 114 and a flat edge 113 on its inner edge as shown. As shown in the figure, beveled edge 108 and half of flat edge 109 are inspected by Detector Optics #1 116, and beveled edge 110 and the other half of flat edge 109 are inspected by Detector Optics #2 118. Detector Optics #1 116 and PATENT Detector Optics #2 118 project the image of the edge to be inspected onto detectors, the outputs of which are processed to determine if any defects occur greater than a programmable threshold. This detection and process step is represented by the Detectors and Process block 124. Any defect in the Outer Radius Inspection Assembly 128 above its programmable threshold is reported to the computer 46 as a fault, which causes the disk inspection to fail.

An obvious modification to the present invention would be to provide an Inner Radius Inspection Assembly with similar construction to the Outer Radius Inspection Assembly. The Projection Optics for this Inner Radius Inspection Assembly would have to be positioned out of the way during loading of Disk 75 into apparatus 40, and then be positioned under control of the computer 46 at the internal edges of the Reflective Disk 75 during inspection, and would then have to be positioned out of the way to allow unloading of the Reflective Disk 75 after inspection. While this is an obvious modification to the apparatus 40 of the present invention, this feature is not shown in the figures.

Figure 7:
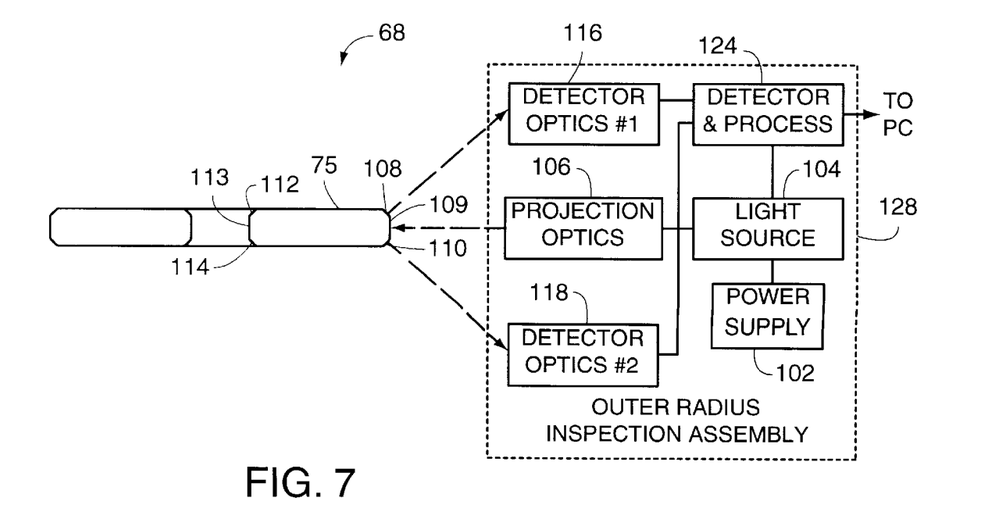
FIG. 7 is a block diagram of the Edge Inspection Assembly portion of the Optical Inspection Assembly shown in FIG. 2.
Figure 8:
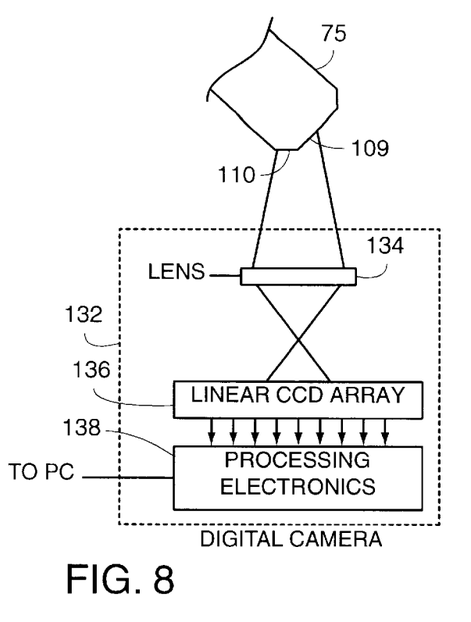
FIG. 8 is a partial perspective view of one particular implementation of the outer radius inspection assembly shown in FIG. 7 using a camera having a linear CCD array.

Many of the components shown in FIG. 7 are also represented in FIG. 3 in their preferred configurations of the present invention. Projection Optics 106 is a fiberoptic strand as represented in FIG. 3. Each of the Detector Optics 116 and 118 are digital CCD cameras in the first embodiment shown in FIG. 3. A detailed view of the operation of one of the digital CCD cameras is shown in FIG. 8. For illustrative purposes, inspection of edge 110 of the Reflective Disk 75 is shown. The digital CCD camera 132 has a single row of CCDs, known as a Linear CCD Array 136. The image of the edge 110 of the Reflective Disk 75 to be inspected is focused by the lens 134 of the camera 132 onto the Linear CCD Array 136 as shown. The Processing Electronics 138 then processes the outputs from the Linear CCD Array 136 and asserts a fault signal to the computer 46 if a defect above a programmable threshold value exists. The Linear CCD Array 136 only detects a small portion of the disk edge as shown in FIG. 8, but the rotation of the disk for one revolution during inspection allows the camera 132 to inspect the entire edge during that one revolution. This occurs simultaneously for edges 108, 109 and 110 as shown in FIG. 7, and occurs simultaneously with the inspection of the surface of the Reflective Disk 75 by the Surface Inspection Assembly 66.

Each inspection assembly in the apparatus 40 of the present invention has its own programmable threshold above which a fault will be signaled, causing the disk inspection to fail. In this manner the computer 46 only has to load the disk, rotate the disk, and monitor the outputs of each inspection assembly for faults. If a fault is signaled to the computer 46 prior to a full revolution being completed, the inspection fails and the disk is unloaded by the Automatic Disk Handler 42 and placed in the place for "bad" disks. If the computer 46 completes a full rotation of the disk with no fault signal from any of the inspection assemblies, the disk passes the inspection and is unloaded by the Automatic Disk Handler 42 and placed in the place for "good" disks.

Figure 9A:
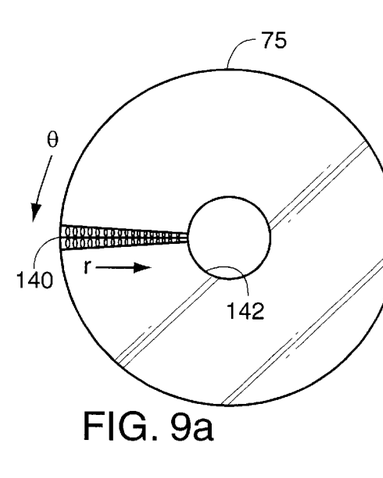
FIG. 9a is a front view of the reflective disk shown in FIG. 3 showing the scanning in the r direction, and rotation of the disk in the theta direction.
Figure 9B:
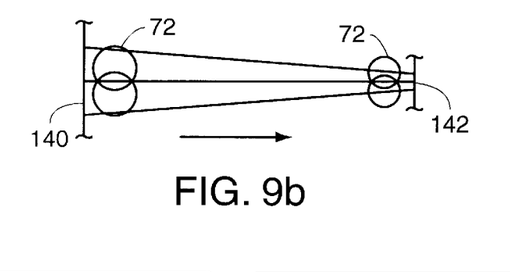
FIG. 9b is an enlarged view of the scanned portion of FIG. 9a showing how the combination of the linear travel of the beam and the rotation of the disk results in complete scanning of the entire surface of the disk.

FIGS. 9a and 9b illustrate how the combination of the scanning of the beam 72 and the rotation of the Reflective Disk 75 provide for a complete inspection of the entire surface of the Reflective Disk 75. As shown in FIG. 9a, the beam 72 scans in a line from left to right as shown by the r direction. At the same time the disk rotates in the theta direction shown in the figure. In this manner the disk is inspected in polar coordinates, with their coordinate representing the position of the beam 72 in its scan path, and the theta coordinate representing the rotational position of the Reflective Disk 75. The effect of this polar scanning technique is shown in FIG. 9b.

The beam is configured to scan along a radius of the Reflective Disk 75, from left to right as shown. The beam has a spot size which travels along this scan path. In order for the beam 72 to completely scan the entire surface of the Reflective Disk 75, the beam 72 must overlap somewhat with the previous scan path. Due to the circular configuration of the disk the outside circumference is significantly greater than the inside circumference, so a rotational change of position causes the outer edge to travel a farther distance than the inner edge. This means that the spot must overlap slightly on the outer edge 140 of the disk, which causes a much greater overlap on the inner edge 142 of the disk, as shown in FIG. 9b. This difference in overlap between the beam at the outer edge 140 and the inner edge 142 of the Reflective Disk 75 can be corrected using electronics or software to provide for accurate mapping of disk defects.

Referring again to FIG. 3, rollers 96, 98 and 100 comprise the Disk Movement Actuator 64 shown in FIG. 2. Only one of these three rollers 96, 98 and 100 are motor-driven, with the computer 46 controlling the motor drive through communicating with the Disk Movement Driver 62 as shown in FIG. 2. For illustration purposes, it will be assumed that roller 96 is the one roller that is driven by a motor, and that it rotates in a clockwise direction as shown. As the Optical Scanner 80 sweeps the beam 72 repeatedly from left to right on a radius of both sides of Reflective Disk 75, the computer 46 causes roller 96 to rotate clockwise, which causes Reflective Disk 75 to rotate counter-clockwise. In this manner the entire surface of Reflective Disk 75 is scanned when it has rotated one revolution.

FIG. 3 shows a lifter 99, which acts in conjunction with the Automatic Disk Handler 42 (not shown) to load untested disks into the Optical Inspection Assembly 52 and to unload tested disks from the Optical Inspection Assembly 52. The detailed operation of the loading and unloading function can be best understood in reference to FIGS. 11a–c. These three figures illustrate how the Reflective Disk 75 is unloaded from the Optical Inspection Assembly 52 by the Gripping Arm 101 of the Automatic Disk Handler 42. FIG. 11a shows a Reflective Disk 75 while it is being rotated under test by rollers 96, 98 and 100. Lifter 99 is positioned away from the Reflective Disk 75 during testing. When testing is complete, the computer 46 stops driving roller 96, causing the rotation of the rollers 96, 98 and 100 to stop. The computer 46 then moves the roller 98 out of the way as shown in FIG. 11b. Once roller 98 is out of the way, the Gripping Arm 101 of Automatic Disk Handler 42 is placed into the proper position, and lifter 99 then lifts the Reflective Disk 75 away from rollers 96 and 98, to a position where Gripping Arm 101 can close and thereby grip the Reflective Disk 75, as shown in FIG. 11c. This process is reversed for loading disks into the Optical Inspection Assembly 52. Figure lid shows a side view of the rollers 98 and 100 and the Reflective Disk 75 shown in FIG. 11a, illustrating the narrow slots or "V" grooves 103 used to hold the Reflective Disk 75 in the proper position on the rollers 96, 98 and 100.

Figure 6:
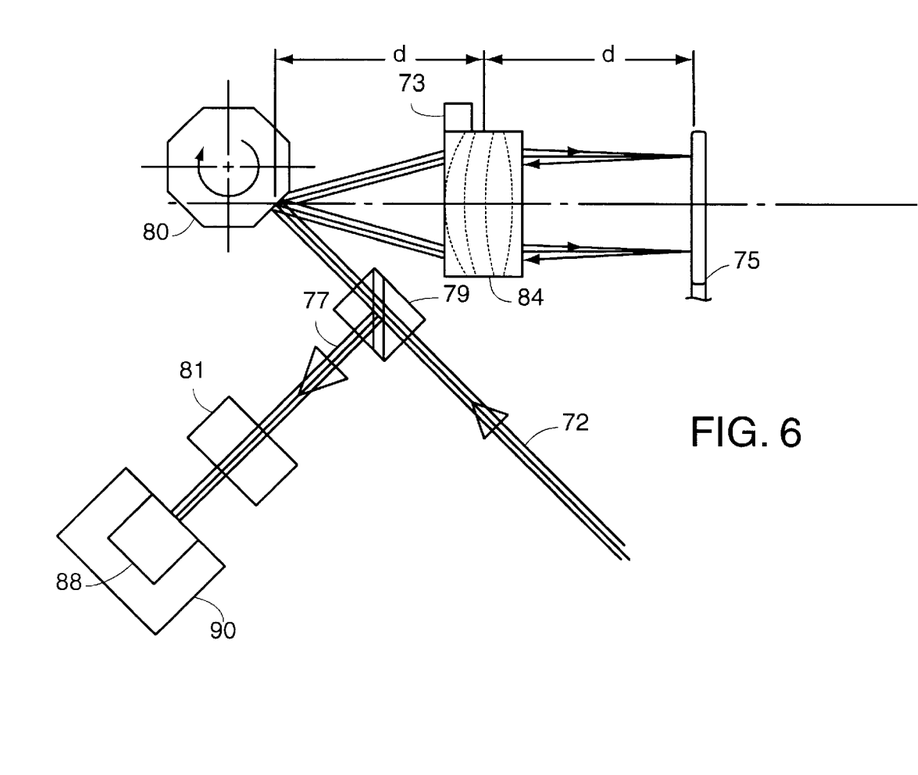
FIG. 6 is a top view of the Optical Scanner and optics function in the Surface Inspection Assembly according to the second embodiment of the apparatus shown in FIG. 1.

As FIGS. 3 and 4 clearly show, the first embodiment allows inspection of both sides of the reflective disk in one scan. In the second embodiment, as shown in FIG. 6, the Surface Inspection Assembly 66 does not have the mirrors that allow the scanning of both sides at once, but the Reflective Disk 75 is inspected one side at a time. When the apparatus 40 completes inspection of one side, it then turns the Reflective Disk 75 and inspects the second side. The operation of all the other features of this second embodiment are identical to those explained in relation to FIGS. 3 and 4. In addition, two separate scanning systems could be used in the configuration shown in FIG. 6 to accomplish scanning of both sides of the Reflective Disk 75 simultaneously.

Figure 13:
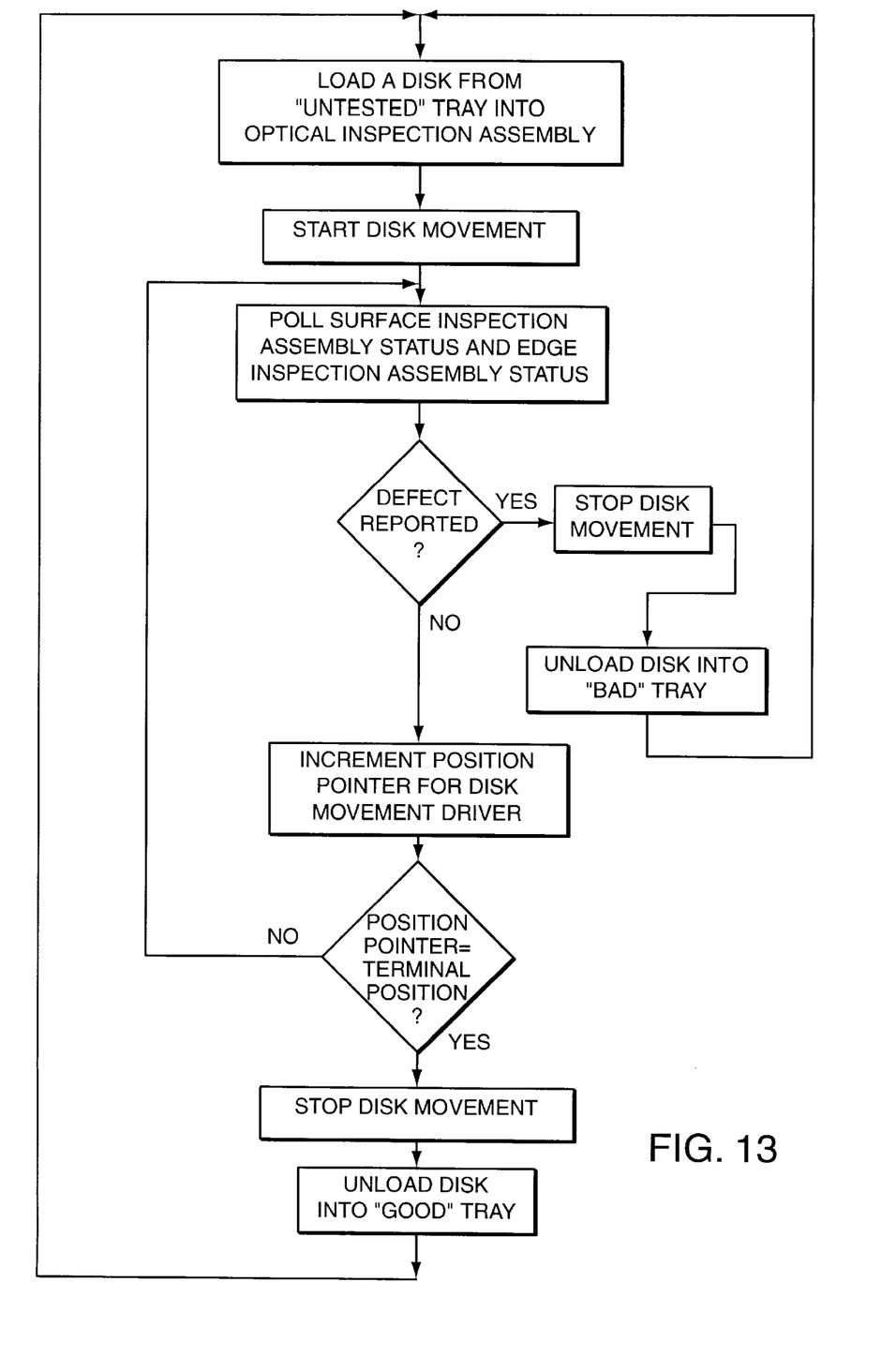
FIG. 13 is a flow chart of the control software operation for the apparatus of the present invention.

The flow chart of the program flow of the control software within computer 46 is shown in FIG. 13. The specific implementation shown in FIG. 13 assumes that the computer 46 will poll the Surface Inspection Assembly 66 and the Edge Inspection Assembly 68 to determine whether a defect is reported by either of these assemblies. In an alternative arrangement, the fault output 93 of the Surface Inspection Assembly 66 and the fault output 93 of the Edge Inspection Assembly 68 are interrupt-driven inputs to computer 46, which report a fault by interrupting program execution of the computer 46. In this configuration the computer 46 simply completes the rotation of the disk, then checks a software flag to determine whether a fault was detected during the scan.

The automation of apparatus 40 provided by computer 46 and Automatic Disk Handler 42 provides for high-speed inspection of apparatus 40, which suits the apparatus 40 well to a speed-sensitive production environment.

While the invention has been described in its preferred embodiments, it is to be understood that the words which have been used are words of description rather than limitation, and that changes may be made within the purview of the appended claims without departing from the true scope and spirit of the invention in its broader aspects.

What is claimed is:

1. An optical inspection apparatus for inspecting a flat, reflective circular disk comprising, in combination:
   computer means for controlling said apparatus;
   operator interface means coupled to said computer means for providing input data from an operator to said computer means and for providing output data from said computer means to said operator;
   an optical inspection assembly, coupled to said computer means having output means for reporting to said computer means results of an inspection performed by said optical inspection assembly, comprising inspection means consisting of detector means for detecting changes of a normal Gaussian distribution of a light beam; and
   a reflective disk which is placed in said optical inspection assembly to inspect said reflective disk for defects.

2. The apparatus of claim 1 further comprising automatic disk handler means coupled to said computer means for loading under control of said computer means said reflective disk into said optical inspection assembly and for unloading under control of said computer means said reflective disk out of said optical inspection assembly.

3. The apparatus of claim 1 wherein said computer means comprising, in combination:
   an IBM compatible personal computer; and
   control software means loaded into memory of said personal computer for determining function and sequence of operations of said apparatus.

4. The apparatus of claim 3 wherein said control software means comprising:
   a main control program; and
   a plurality of device drivers which provide subroutines for said main control program and which control individual components of said apparatus.

5. The apparatus of claim 1 wherein said computer means periodically polls said output means of said optical inspection assembly to determine whether a defect has been detected by said optical inspection assembly.

6. The apparatus of claim 1 wherein said output means of said optical inspection means is coupled to said computer means such that said output means interrupts said computer means when a defect is detected by said optical inspection assembly.

7. The apparatus of claim 1 wherein said operator interface means comprising, in combination:
   keyboard means coupled to said computer means for providing said input data from said operator to said computer means; and
   display means coupled to said computer means for displaying said output data from said computer means to said operator.

8. The apparatus of claim 7 wherein said operator interface means further comprising printer means for printing said output data from said computer means.

9. The apparatus of claim 7 wherein said operator interface means further comprising operator panel means having knobs and switches for selecting one of a plurality of detection thresholds for said optical inspection assembly.

10. The apparatus of claim 7 including means for permitting said operator to select one of a plurality of detection thresholds for said optical inspection assembly via said keyboard means.

11. The apparatus of claim 2 wherein said automatic disk handler means comprising, in combination:
    at least one input tray wherein said reflective disk is placed prior to inspection by said apparatus;
    at least one movable gripper hand located in proximity to said input tray for gripping and transporting said reflective disk from said input tray to said optical inspection assembly;
    a first output tray located in proximity to said movable gripper hand such that said reflective disk is moved from said optical inspection assembly to said first output tray by said movable gripper hand if said output of said optical inspection assembly signals to said computer means that said reflective disk has no defects; and
    a second output tray located in proximity to said movable gripper hand such that said reflective disk is moved from said optical inspection assembly to said second output tray by said movable gripper hand if said output of said optical inspection assembly signals to said computer means that said reflective disk has defects.

12. The apparatus of claim 1 wherein said optical inspection assembly comprising, in combination:
    disk movement actuator means in physical proximity to said inspection means for moving said reflective disk to allow said inspection means to fully inspect said reflective disk for defects; and
    disk movement driver means electrically coupled to said disk movement actuator means and to said computer means for allowing said computer means to control said disk movement actuator means by providing appropriate commands to said disk movement driver means.

13. The apparatus of claim 12 wherein said inspection means comprises surface inspection assembly means for inspecting at least one flat surface of said reflective disk for defects while said disk movement actuator means moves said unit under test.

14. The apparatus of claim 13 wherein said inspection means further comprises edge inspection assembly means in Physical proximity to said surface inspection assembly means for inspecting at least one edge of said reflective disk for defects while said disk movement actuator means moves said reflective disk.

15. The apparatus of claim 14 wherein said edge inspection assembly means comprising an outer radius inspection assembly for inspecting at least one outer edge of said reflective disk.

16. The apparatus of claim 15 wherein said outer radius inspection assembly comprising, in combination:
    a light source;
    power supply means electrically coupled to said light source for providing power to said light source;
    projection means optically coupled to said light source for projecting said light source onto at least one outer edge of said reflective disk, thereby creating an illuminated portion; and at least one detection means for monitoring said illuminated portion, having output means for reporting the existence of defects in said illuminated portion.

17. The apparatus of claim 16 wherein said detection means further comprising:

a linear array of optical detectors; and detection optics for directing and projecting an image of said illuminated portion to said linear array.

18. The apparatus of claim 17 wherein said optical detectors comprising Charge-Coupled Devices (CCDs).

19. The apparatus of claim 12 wherein said reflective disk comprising a round disk having an outer edge and a hole in a center portion and wherein said disk movement actuator means comprising at least one actuated roller and motor means for driving said actuated roller for turning said round disk.

20. The apparatus of claim 19 wherein said disk movement actuator means further comprising at least one idler roller, said idler roller and said actuated roller contact said outer edge of said round disk, said actuated roller rotating in response to said motor driving said actuated roller causing rotation of said round disk, said rotation of said disk causing said idler roller to rotate.

21. The apparatus of claim 20 wherein said actuated roller and said idler roller both having notch means in their circumferential faces in which said outer edge of said round disk is placed for preventing said round disk from slipping off said actuated roller and said idler roller during rotation.

22. The apparatus of claim 13 wherein said surface inspection assembly means comprising, in combination:

a light source providing said light beam;

optical scanner means in physical proximity to said light source for permitting said light beam to contact said optical scanner means and for reflecting said light beam thereby providing a linear sweep of said light beam;

scanning optics means having a front face portion and a rear face portion for permitting said linear sweep of said light beam to contact said front face portion of said scanning optics means for causing said light beam that contacts said front face portion to exit said rear face portion and to contact said flat surface of said reflective disk, said reflective disk reflecting said light beam back to said scanning optics means in a path coincident with said light beam being directed to said reflective disk;

trigger detector means coupled to said computer means and placed within said linear sweep of said light beam for providing a synchronizing electrical signal to said computer means for indicating a position of said light beam along said linear sweep;

beam splitter means through which said light beam passes for separating said light beam being reflected by said reflective disk from said light beam being directed to said reflective disk;

said detector means for receiving said light beam from said beam splitter means and for detecting changes of a nominal Gaussian distribution of said light beam, said changes corresponding to and identifying defects in said flat surface of said reflective disk.

23. The apparatus of claim 22 wherein said light source comprising a laser diode and said light beam comprising a laser beam from said laser diode.

24. The apparatus of claim 22 wherein said light source comprising a helium-neon laser, and said light beam comprising a laser beam from said helium-neon laser.

25. The apparatus of claim 22 wherein said optical scanner means having a motor-driven polygonal head coupled to said computer means and having reflective faces such that said light beam contacts said reflective faces of said polygonal head, and having means for rotating said polygonal head causing said light beam reflected off said reflective faces to create said linear sweep of said light beam across said scanning optics means.

26. The apparatus of claim 25 wherein said motor-driven polygonal head is turned on and off by said computer means.

27. The apparatus of claim 22 wherein said optical scanner means being located at a distance from said scanning optics means equal to the focal length of said scanning optics means.

28. The apparatus of claim 27 wherein said scanning optics means direct said light beam entering said front face portion such that said light beam exits said rear face portion in a direction normal to the focal plane of said scanning optics means.

29. The apparatus of claim 22 wherein said surface inspection assembly further comprising first and second mirror means placed in said linear sweep of said light beam at an angle for reflecting said light beam from said scanning optics means to said reflective disk and for reflecting said light beam reflected off said reflective disk to said scanning optics means in a path coincident with said light beam directed to said reflective disk, said first mirror means reflecting said light beam onto a first flat surface of said reflective disk, and said second mirror means reflecting said light beam onto a second flat surface of said reflective disk, for permitting said first flat surface and said second flat surface to both be contacted by said light beam during said linear sweep.

30. The apparatus of claim 22 wherein said trigger detector means comprising an optical sensor having an electrical output corresponding to the presence of said light beam on said optical sensor which is coupled to said computer means.

31. The apparatus of claim 30 wherein said optical sensor comprising a photodiode.

32. The apparatus of claim 30 wherein said optical sensor comprising a charge-coupled device (CCD).

33. The apparatus of claim 22 wherein said detector means comprising, in combination:

at least two optical detectors having electrical outputs, said optical detectors functioning in parallel; and electronic circuitry means for processing said electrical outputs of said optical detectors and generating an electrical signal to said computer means comprising, in combination:

first input means coupled to said electrical outputs of said optical detectors for monitoring said electrical outputs;

second input means coupled to said computer means for receiving a threshold value from said computer means;

processing means coupled to said first input means and to said second input means for measuring said electrical outputs of said optical detectors and for determining the existence of changes of said nominal Gaussian distribution of said light beam above said threshold value on said second input means; and output means coupled to said computer means for signaling an occurrence of a change above said threshold value to said computer means.

34. The apparatus of claim 33 wherein said optical detectors comprise photodiodes.

35. The apparatus of claim 33 wherein said optical detectors comprise charge-coupled devices (CCDs).

36. The apparatus of claim 33 wherein said optical detectors are arranged in rows and columns to form a substantially square matrix.

37. The apparatus of claim 33 wherein said optical detectors are arranged in a series of concentric circular rings.

38. The apparatus of claim 22 further comprising filter optics means for increasing spatial coherence of said light beam.

39. A method for inspecting a flat, reflective disk using an optical inspection apparatus including the steps of:
- providing computer means for controlling said apparatus;
- providing operator interface means coupled to said computer means for providing input data from an operator to said computer means and for providing output data from said computer means to said operator;
- providing an optical inspection assembly coupled to said computer means having output means for reporting to said computer means results of an inspection performed by said optical inspection assembly, comprising inspection means consisting of detector means for detecting chances of a nominal Gaussian distribution of a light beam; and
- providing a reflective disk which is placed in said optical inspection assembly to inspect said reflective disk for defects.

40. The method of claim 39 further comprising the step of providing automatic disk handler means coupled to said computer means for loading under control of said computer means said reflective disk into said optical inspection assembly and for unloading under control of said computer means said reflective disk out of said optical inspection assembly.

41. The method of claim 39 wherein said computer means comprising, in combination:
- an IBM compatible personal computer; and
- control software means loaded into memory of said IBM personal computer for determining function and sequence of operations of said apparatus.

42. The method of claim 39 wherein said computer means periodically polls said output means of said optical inspection assembly to determine whether a defect has been detected by said optical inspection assembly.

43. The method of claim 39 wherein said output means of said optical inspection means is coupled to said computer means such that said output means interrupts said computer means when a defect is detected by said optical inspection assembly.

44. The method of claim 39 wherein said operator interface means comprising, in combination:
- keyboard means coupled to said computer means for providing said input data from said operator to said computer means; and
- display means coupled to said computer means for displaying said output data from said computer means to said operator.

45. The method of claim 44 wherein said operator interface means further comprising operator panel means having knobs and switches for selecting one of a plurality of detection thresholds for said optical inspection assembly.

46. The method of claim 44 including means for permitting said operator to select one of a plurality of detection thresholds for said optical inspection assembly via said keyboard means.

47. The method of claim 40 wherein said automatic disk handler means comprising, in combination:
- at least one input tray wherein said reflective disk is placed prior to inspection by said apparatus;
- at least one movable gripper hand located in proximity to said input tray for gripping and transporting said reflective disk from said input tray to said optical inspection assembly;
- a first output tray located in proximity to said movable gripper hand such that said reflective disk is moved from said optical inspection assembly to said first output tray by said movable gripper hand if said output of said optical inspection assembly signals to said computer means that said reflective disk has no defects; and
- a second output tray located in proximity to said movable gripper hand such that said reflective disk is moved from said optical inspection assembly to said second output tray by said movable gripper hand if said output of said optical inspection assembly signals to said computer means that said reflective disk has defects.

48. The method of claim 39 wherein said optical inspection assembly comprising, in combination:
- disk movement actuator means in physical proximity to said inspection means for moving said reflective disk to allow said inspection means to fully inspect said reflective disk for defects; and
- disk movement driver means electrically coupled to said disk movement actuator means and to said computer means for allowing said computer means to control said disk movement actuator means by providing appropriate commands to said disk movement driver means.

49. The method of claim 48 wherein said inspection means comprises surface inspection assembly means for inspecting at least one flat surface of said reflective disk for defects while said disk movement actuator means moves said reflective disk.

50. The method of claim 49 wherein said inspection means further comprises edge inspection assembly means in physical proximity to said surface inspection assembly means for inspecting at least one edge of said reflective disk for defects while said disk movement actuator means moves said reflective disk.

51. The method of claim 48 wherein said reflective disk comprising a round disk having an outer edge and a hole in a center portion and wherein said disk movement actuator means comprising at least one actuated roller and motor means for driving said actuated roller for turning said round disk.

52. The method of claim 51 wherein said disk movement actuator means further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

53. The method of claim 52 wherein said actuated roller and said idler roller both having notch means in their circumferential faces in which said outer edge of said round disk is placed for preventing said round disk from slipping off said actuated roller and said idler roller during rotation.

54. The method of claim 49 wherein said surface inspection assembly means comprising, in combination:
- a light source providing said light beam;
- optical scanner means in physical proximity to said light source for permitting said light beam to contact said optical scanner means and for reflecting said light beam thereby providing a linear sweep of said light beam;
- scanning optics means having a front face portion and a rear face portion for permitting said linear sweep of said light beam to contact said front face portion of said scanning optics means for causing said light beam that contacts said front face portion to exit said rear face portion and to contact said flat surface of said reflective disk, said reflective disk reflecting said light beam back to said scanning optics means in a path coincident with said light beam being directed to said reflective disk;

trigger detector means coupled to said computer means and placed within said linear sweep of said light beam for providing a synchronizing electrical signal to said computer means for indicating a position of said light beam along said linear sweep;

beam splitter means through which said light beam passes for separating said light beam being reflected by said reflective disk from said light beam being directed to said reflective disk;

said detector means for receiving said light beam from said beam splitter means and for detecting changes of a nominal Gaussian distribution of said light beam, said changes corresponding to and identifying defects in said flat surface of said reflective disk.

55. The method of claim 54 wherein said optical scanner means having a motor-driven polygonal head coupled to said computer means and having reflective faces such that said light beam contacts said reflective faces of said polygonal head, and having means for rotating said polygonal head for causing said light beam reflected off said reflective faces to create said linear sweep of said light beam across said scanning optics means.

56. The method of claim 55 wherein said motor-driven polygonal head is turned on and off by said computer means.

57. The method of claim 54 wherein said optical scanner means being located at a distance from said scanning optics means equal to the focal length of said scanning optics means.

58. The method of claim 57 wherein said scanning optics means direct said light beam entering said front face portion such that said light beam exits said rear face portion in a direction normal to the focal plane of said scanning optics means.

59. The method of claim 54 wherein said surface inspection assembly further comprising first and second mirror means placed in said linear sweep of said light beam at an angle for reflecting said light beam from said scanning optics means to said reflective disk and for reflecting said light beam reflected off said reflective disk to said scanning optics means in a path coincident with said light beam directed to said reflective disk, said first mirror means reflecting said light beam onto a first flat surface of said reflective disk, and said second mirror means reflecting said light beam onto a second flat surface of said reflective disk, for permitting said first flat surface and said second flat surface to both be contacted by said light beam during said linear sweep.

60. The method of claim 54 wherein said trigger detector means comprising an optical sensor having an electrical output corresponding to the presence of said light beam on said optical sensor which is coupled to said computer means.

61. The method of claim 54 wherein said detector means comprising, in combination:

at least two optical detectors having electrical outputs, said optical detectors functioning in parallel; and electronic circuitry means for processing said electrical outputs of said optical detectors and generating an electrical signal to said computer means comprising, in combination:

first input means coupled to said electrical outputs of said optical detectors for monitoring said electrical outputs;

second input means coupled to said computer means for receiving a threshold value from said computer means;

processing means coupled to said first input means and to said second input means for measuring said electrical outputs of said optical detectors and for determining the existence of changes of said nominal Gaussian distribution of said light beam above said threshold value on said second input means; and output means coupled to said computer means for signaling an occurrence of a change above said threshold value to said computer means.

62. The method of claim 61 wherein said optical detectors are arranged in rows and columns to form a substantially square matrix.

63. The method of claim 61 wherein said optical detectors are arranged in a series of concentric circular rings.

64. The method of claim 47 further comprising the steps of:

loading said reflective disk into said disk movement actuator means in said optical inspection assembly;

activating said surface inspection assembly means with said computer means;

said computer means providing commands to said disk movement driver means, thereby causing said disk movement actuator means to rotate said reflective disk such that the entirety of said flat surface is inspected;

checking with said computer means said output of said optical inspection assembly to determine whether a defect was detected by said optical inspection assembly; and unloading said reflective disk from said optical inspection assembly into a first destination if said output on said optical inspection assembly did not indicate the presence of a defect on said reflective disk, and unloading said reflective disk from said optical inspection assembly into a second destination if said output of said optical inspection assembly did indicate the presence of a defect on said reflective disk.

65. An apparatus for optically scanning the flat portions of a reflective disk comprising, in combination:

a light source providing a light beam;

light beam reflecting means for reflecting said light beam for providing a linear sweep of said light beam;

a reflective disk having a flat surface to be inspected positioned in said linear sweep of said light beam;

detector means for receiving said light beam and for detecting changes of a nominal Gaussian distribution of said light beam corresponding to defects in said flat surface of said reflective disk; and means for moving said reflective disk within said linear sweep of said light beam and for permitting a linear scan of said flat surface for complete scanning of all of said flat surface to be inspected.

66. The apparatus of claim 65 wherein said light source comprising a laser diode and said light beam comprising a laser beam from said laser diode.

67. The apparatus of claim 65 wherein said light source comprising a helium-neon laser, and said light beam comprising a laser beam from said helium-neon laser.

68. The apparatus of claim 65 wherein said light beam reflecting means comprising an optical scanner.

69. The apparatus of claim 68 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

70. The apparatus of claim 65 wherein said reflective disk comprising a round disk having an outer edge and a hole in a center portion and wherein said means for moving said reflective disk comprising at least one actuated roller and motor means for driving said actuated roller for turning said round disk.

71. The apparatus of claim 70 wherein said means for moving said reflective disk further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

72. The apparatus of claim 71 wherein said actuated roller and said idler roller both having notch means in their circumferential faces in which said outer edge of said round disk is placed for preventing said round disk from slipping off said actuated roller and said idler roller during rotation.

73. A method for optically scanning the flat surface of a reflective disk comprising, in combination:
    providing a light source having a light beam;
    providing light beam reflecting means for reflecting said light beam for providing a linear sweep of said light beam;
    providing a reflective disk having a flat surface to be inspected positioned in said linear sweep of said light beam;
    providing detector means for receiving said light beam and for detecting changes of a nominal Gaussian distribution of said light beam corresponding to defects in said flat surface of said reflective disk; and
    providing means for moving said reflective disk within said linear sweep of said light beam and for permitting a linear scan of said flat surface for complete scanning of all of said flat surface to be inspected.

74. The method of claim 73 wherein said light beam reflecting means comprising an optical scanner.

75. The method of claim 74 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

76. The method of claim 73 wherein said means for moving said reflective disk comprising at least one actuated roller and motor means for driving said actuated roller for turning said reflective disk.

77. The method of claim 76 wherein said means for moving said reflective disk further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

78. The method of claim 77 wherein said actuated roller and said idler roller both having notch means in their circumferential faces in which said outer edge of said round disk is placed for preventing said round disk from slipping off said actuated roller and said idler roller during rotation.

79. The method of claim 73 further comprising the steps of:
    placing said reflective disk into said means for moving said reflective disk; and
    activating said means for moving said reflective disk causing all of said flat surface to pass through said linear sweep of said light beam.

80. An apparatus for detecting surface defects in the flat surface of a reflective disk comprising, in combination:
    a light source providing a light beam;
    light beam reflecting means for reflecting said light beam for providing a linear sweep of said light beam;
    a reflective disk having a flat surface to be inspected positioned in said linear sweep of said light beam;
    means for moving said reflective disk within said linear sweep of said light beam and for permitting a linear scan of said flat surface for complete scanning of all of said flat surface to be inspected; and
    detector means for measuring changes in said light beam corresponding to defects on said flat surface of said reflective disk, wherein said detector means receives said light beam and detects changes of a nominal Gaussian distribution of said light beam, said changes corresponding to defects in said flat surface of said reflective disk.

81. The apparatus of claim 80 wherein said light source comprising a laser diode and said light beam comprising a laser beam from said laser diode.

82. The apparatus of claim 80 wherein said light source comprising a helium-neon laser, and said light beam comprising a laser beam from said helium-neon laser.

83. The apparatus of claim 80 wherein said light beam reflecting means comprising an optical scanner.

84. The apparatus of claim 83 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

85. The apparatus of claim 80 wherein said reflective disk comprising a round disk having an outer edge and a hole in a center portion and wherein said means for moving said reflective disk comprising at least one actuated roller and motor means for driving said actuated roller for turning said round disk.

86. The apparatus of claim 85 wherein said means for moving said reflective disk further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

87. The apparatus of claim 86 wherein said actuated roller and said idler roller both having notch means in their circumferential faces in which said outer edge of said round disk is placed for preventing said round disk from slipping off said actuated roller and said idler roller during rotation.

88. The apparatus of claim 80 wherein said detector means comprising, in combination:
    at least two optical detectors having electrical outputs, said optical detectors functioning in parallel; and
    electronic circuitry means for processing said electrical outputs of said optical detectors and generating an electrical signal output in response to changes of a nominal Gaussian distribution of said light beam above a selectable threshold value.

89. A method for detecting surface defects in the flat surface of a reflective disk comprising, in combination:
    providing a light source having a light beam;
    providing light beam reflecting means for reflecting said light beam for providing a linear sweep of said light beam;

providing a reflective disk having a flat surface to be inspected positioned in said linear sweep of said light beam;

providing means for moving said reflective disk within said linear sweep of said light beam and for permitting a linear scan of said flat surface for complete scanning of all of said flat surface to be inspected; and providing detector means for measuring changes in said light beam corresponding to defects on said flat surface of said reflective disk, wherein said detector means receives said light beam and detects changes of a nominal Gaussian distribution of said light beam, said changes corresponding to defects in said flat surface of said unit test.

90. The method of claim 89 wherein said light beam reflecting means comprising an optical scanner.

91. The method of claim 90 wherein said optical scanner having a motor-driven polygonal head having reflective faces positioned to permit said light beam to contact said reflective faces of said polygonal head, and having means for rotating said polygonal head for causing said light beam reflected off said reflective faces to create said linear sweep of said light beam.

92. The method of claim 89 wherein said reflective disk comprising a round disk having an outer edge and a hole in a center portion and wherein said means for moving said reflective disk comprising at least one actuated roller and motor means for driving said actuated roller for turning said round disk.

93. The method of claim 92 wherein said means for moving said reflective disk further comprising at least one idler roller, said idler roller and said actuated roller contact said outer edge of said round disk, said actuated roller rotating in response to said motor means driving said actuated roller causing rotation of said round disk, said rotation of said disk causing said idler roller to rotate.

94. The method of claim 93 wherein said actuated roller and said idler roller both having notch means in their circumferential faces in which said outer edge of said round disk is placed for preventing said round disk from slipping off said actuated roller and said idler roller during rotation.

95. The method of claim 89 wherein said detector means comprising, in combination:

at least two optical detectors having electrical outputs, said optical detectors functioning in parallel; and electronic circuitry means for processing said electrical outputs of said optical detectors and generating an electrical signal output in response to changes of a nominal Gaussian distribution of said light beam above a selectable threshold value.

96. The method of claim 89 further comprising the steps of:

placing said reflective disk into said means for moving said reflective disk;

activating said means for moving said reflective disk causing all of said flat surface to pass through said linear sweep of said light beam; and activating said detector means.

* * * * *